United States Patent [19]
Jean et al.

[11] Patent Number: 5,331,284
[45] Date of Patent: Jul. 19, 1994

[54] METER AND METHOD FOR IN SITU MEASUREMENT OF THE ELECTROMAGNETIC PROPERTIES OF VARIOUS PROCESS MATERIALS USING CUTOFF FREQUENCY CHARACTERIZATION AND ANALYSIS

[75] Inventors: Buford R. Jean, Round Rock, Tex.; Gary L. Warren, Cranford, Conn.; F. Lynn Whitehead, Austin, Tex.

[73] Assignee: Baker Hughes Incorporated, Houston, Tex.

[21] Appl. No.: 871,339

[22] Filed: Apr. 21, 1992

[51] Int. Cl.$^5$ .................. G01N 22/04; G01R 27/04
[52] U.S. Cl. .................. 324/639; 324/640; 324/636; 364/484
[58] Field of Search ............ 324/633, 634, 636, 637, 324/639, 640, 641; 364/481, 484, 485, 499, 553

[56] References Cited

U.S. PATENT DOCUMENTS

| | | | |
|---|---|---|---|
| 2,659,860 | 11/1953 | Breazeale | 324/49 |
| 3,500,182 | 3/1970 | Reed et al. | 324/58.5 |
| 3,612,996 | 8/1969 | Bleackley | 324/58.5 A |
| 3,818,333 | 6/1974 | Walker | 324/58.5 A |
| 3,946,308 | 3/1976 | Miura et al. | 324/58.5 C |
| 4,042,879 | 8/1977 | Ho et al. | 324/58.5 C |
| 4,211,970 | 7/1980 | Fitzky et al. | 324/58.5 C |
| 4,258,423 | 3/1981 | Lane et al. | 364/484 |
| 4,301,400 | 11/1981 | Paap | 324/58.5 A |
| 4,365,503 | 12/1982 | Ho et al. | 73/3 |
| 4,379,991 | 4/1983 | Ho et al. | 324/58.5 C |
| 4,423,623 | 1/1984 | Ho et al. | 73/61 R |
| 4,546,311 | 10/1985 | Knöchel | 324/58.5 R |
| 4,559,493 | 12/1985 | Goldberg et al. | 324/61 R |
| 4,580,233 | 4/1986 | Parker et al. | 364/550 |
| 4,614,721 | 9/1986 | Goldberg | 436/147 |
| 4,675,595 | 6/1987 | Hane | 324/58.5 B |
| 4,739,249 | 4/1988 | Nyfors et al. | 324/58.5 C |
| 4,755,743 | 7/1988 | Jakkula | 324/640 X |
| 4,764,718 | 8/1988 | Revus et al. | 324/58.5 A |
| 4,767,982 | 8/1988 | Florig et al. | 324/58.5 A |
| 4,789,820 | 12/1988 | Parrent, Jr. et al. | 324/58.5 R |

(List continued on next page.)

OTHER PUBLICATIONS

"Digital High/Low-Pass Filter Features Voltage-Adjustable Cut-Off Points"-Black Michael F.

(List continued on next page.)

Primary Examiner—Gerard R. Strecker
Assistant Examiner—Diep Do
Attorney, Agent, or Firm—Alton W. Payne

[57] ABSTRACT

An apparatus and method for the measurement of, for example, the moisture in a material or, more generally, for the measurement of any material parameter which may be inferred by measuring the electromagnetic properties of the material under investigation. The meter apparatus comprises a controllable source of electromagnetic energy having stable selectable frequency. The controllable source of electromagnetic energy is coupled to a material measurement chamber by means of probes, loops, antennas, apertures or other structures so as to establish an electromagnetic field inside the measurement chamber thereby causing the field to interact with the material contained in the chamber. The method includes passing the process material through a frequency sensitive measurement cell. Exposing the process material to electromagnetic energy produced by a multi-frequency source. Generating an output signal having a distinctive frequency response characteristic. Detecting and amplifying an output signal by a receiving means and converting the signal to a digital representation. Analyzing the digital representation of the signal by the computer to determine the cutoff frequency. Determining the sharpness of the cutoff characteristic by mathematical algorithms in the computer. From the measured cutoff frequency and the sharpness of the cutoff characteristic, determining the dielectric constant and the conductivity of the material. Using stored calibration data or equations in the computer, computing and displaying the desired material property, e.g., the material's moisture content. And further, using the passband attenuation to determine the density of the material.

2 Claims, 12 Drawing Sheets

U.S. PATENT DOCUMENTS

| | | | |
|---|---|---|---|
| 4,812,739 | 3/1989 | Swanson | 324/58.5 A |
| 4,862,060 | 8/1989 | Scott et al. | 324/58.5 A |
| 4,888,547 | 12/1989 | McGinn et al. | 324/58.5 A |
| 4,902,961 | 2/1990 | De et al. | 324/640 |
| 4,962,384 | 10/1990 | Walker | 324/640 X |
| 4,996,490 | 2/1991 | Scott et al. | 324/639 |
| 5,101,163 | 3/1992 | Agar | 324/639 |
| 5,124,653 | 6/1992 | Andersen et al. | 324/633 X |

OTHER PUBLICATIONS

"Bandwidth and Cut-Off Wavelength of Single-Mode Lightguide-System Considerations"–Tarwater, et al.

"A Frequency Selective Power Meter for Millimeter Waves"–Long, M. W.

"Some Basic Considerations Concerning the Time-Domain Measurements with Electromagnetic-Field Sensors"–Klaasen, J. J.

"Small Band Gap Superlattices as Intrinsic Long Wavelength Infrared Detector Materials"–Smith, D. L.

"Advanced Light Source Storage Ring RF System"–Taylor, B.

"Finite Element Analysis of Waveguides"–INSPEC: Information Services for the Physics and Engineering Communities Database.

"Effective Cut-Off Wavelength for Single-Mode Fibers: The Combined Effect or Curvature and Indes Profile"–Shah, V. S.

"Propagation of Bending Waves in a Periodically Stiffened Panel"–Goeransson, P.

"Evanescent Resonator Frequency Multiplier" (Patent Application)–Hartley, J. H.

"Millimeter-Wave Cut-Off Switch" (Patent Application)–Stern, Richard A.

"On-Line Microwave Monitor for Solid Concentration in Coal-Water Sluries"–Goldberg, et al.

"Dispersion and Cut-Off Phenomena in Rods and Beams"–Junger, Miguel C.

"Modal Characteristics of Quadruple-Ridged Circular and Square Waveguides"–Chen, Ming H.

"The Computation of Waveguide Fields and Cut-Off Frequencies Using Finite Difference Techniques"–Sinnott, D. H.

"Corroborating Cutoff Frequency Measurements with DC Gain Measurements"–Jenkins, K. A.

"Pulse Generator with Symmetrical Output for EMP-/EMC Measurements"–Kruse, K. D.

"Antennas and Accessories"–Hoahn, Alfred J.

"A Note on Cutoff Frequency of TE//01 Mode in TEM Cells"–Zhang, Jingiun.

"Characteristics of a Single-Mode Fiber Beyond the Cutoff Frequency of the LP//1//1 Mode"–Hirantani, Yuji.

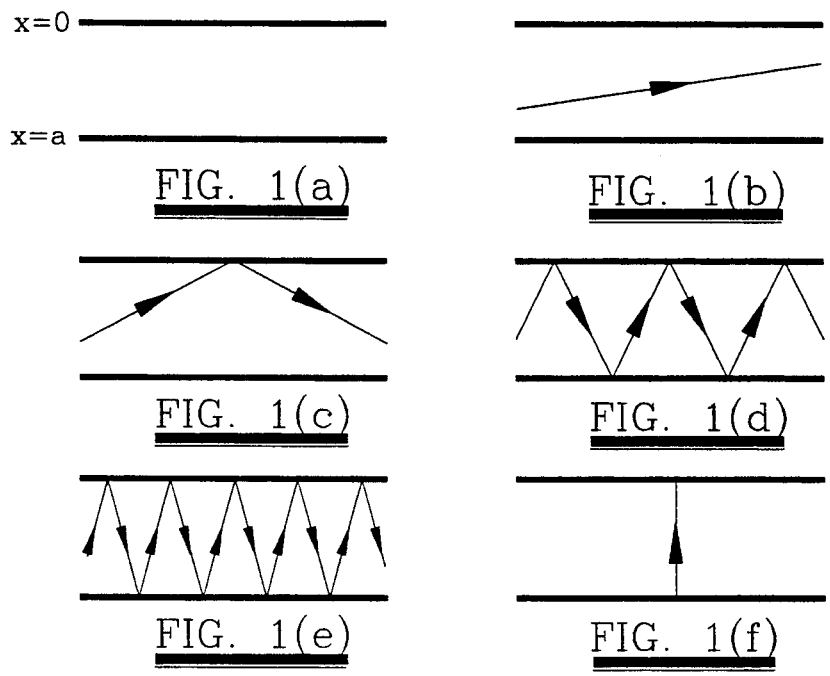
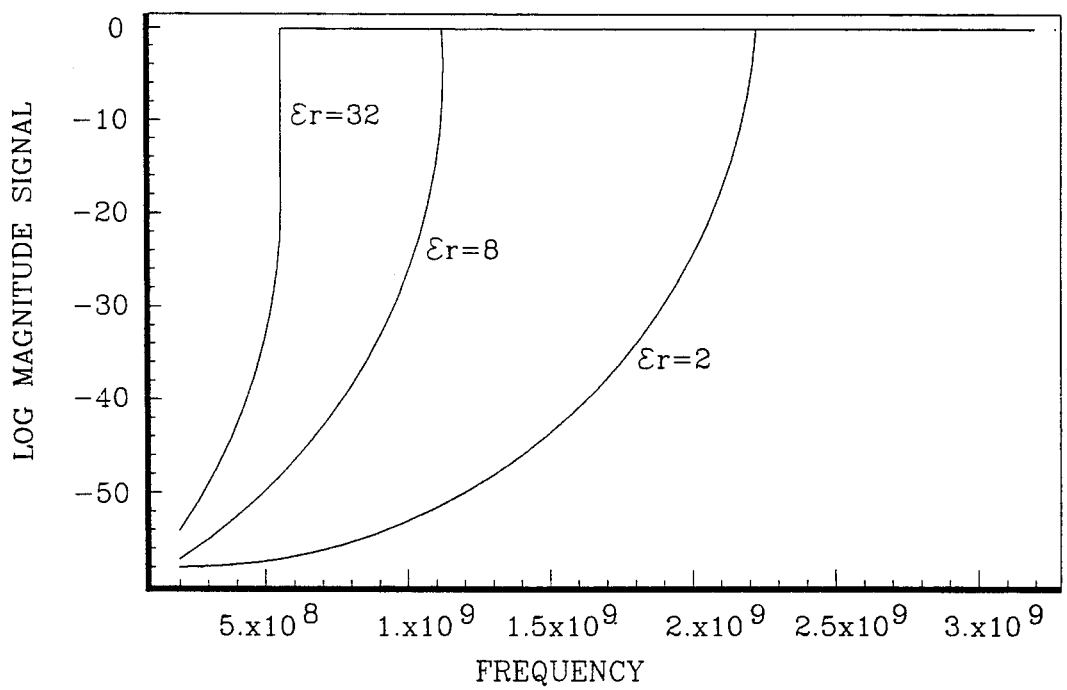

FREQUENCY

FREQUENCY

METER AND METHOD FOR IN SITU MEASUREMENT OF THE ELECTROMAGNETIC PROPERTIES OF VARIOUS PROCESS MATERIALS USING CUTOFF FREQUENCY CHARACTERIZATION AND ANALYSIS

FIELD OF THE INVENTION

The present invention relates generally to the in situ measurement of the electromagnetic properties, i.e., the complex electric permittivity or magnetic permeability, of a wide range of process materials or, more generally, to the measurement of any material parameter that may be inferred from measuring the electromagnetic properties of the material. Of particular interest is the measurement of the amount of moisture in a material. More specifically, the present invention relates to microwave apparatus and method for making such measurements.

BACKGROUND OF THE INVENTION

It is well known to use microwave apparatus for measuring the dielectric of materials which corresponds to the content of moisture or water within the material. For example, Scott and Yang, in U.S. Pat. Nos. 4,996,490 and 4,862,062, describe a microwave apparatus and method for measuring fluid mixtures. The Scott and Yang device and method utilizes a coaxial microwave transmission line, a free-running voltage controlled oscillator and a signal receiver for monitoring the change in frequency caused by impedance pulling of the oscillator due to the change in the dielectric constant of the mixture.

De, et al., in U.S. Pat. No. 4,902,961, describe a microwave system for monitoring the content of water in a petroleum pipe line. The De, et al. apparatus and method uses an S-band antenna and an X-band antenna to determine the complex dielectric constant of the fluid in the pipe line. The overall water content of the pipe line can be determined using an S-band main link that transmits a wave through a representative portion of the entire pipeline. Similarly, Swanson, in U.S. Pat. No. 4,812,739, describes an apparatus and method for using microwave radiation to measure the content of water in a fluid. The volume fraction of water in the fluid is measured by using first and second microwave beams having different frequencies. The beams are transmitted through the liquid and their respective absorption losses are calculated. The volume fraction of water is determined according to the absorption losses.

Several moisture measuring devices and methods are also known. For example, Knochel, in U.S. Pat. No. 4,546,311, describes a device for measuring moisture content. The Knochel patent uses microwaves produced by a transmitting arrangement formed by a signal source and antenna. The moisture laden substance is exposed to the field of radiation. An evaluation arrangement is connected to receive a phase change of the transmitted signal. The phase change represents the moisture content of the substance. Also, Read, in U.S. Pat. No. 3,500,182, describes an apparatus and method for the measurement of moisture in highly viscous pastes and similar materials. The Read patent measures moisture by passing high frequency electromagnetic signals through the viscous material. The viscous material is constrained in a chamber having a pair of opposed boundary plates extending edge-on in the direction of the movement of the material to form a combining guide path for the signals. The signals are evaluated before and after traversing the material to determine the moisture content in the material.

Bleackley, in U.S. Pat. No. 3,612,996, describes the measurement of the constituent proportions of a flowing substance using microwave energy. A method and apparatus are described having a main section wave guide, a branch section wave guide and a window. The three components make up a wave guide configuration which is a resonant microwave structure. The moisture in the material is determined by the resonant frequency of the structure. Also, Walker, in U.S. Pat. No. 3,818,333, describes a microwave window and antenna for measuring moisture of fluidized material. The described microwave windows extend parallel to each other and perpendicular to the axis of the microwave beam used. The antennas are in the form of dielectric rods. Ho, et al., in U.S. Pat. No. 4,423,623, describe a meter and method for measuring the composition and flow rate of a coal slurry and other similar mixtures. Signals are processed to determine a characteristic frequency of the waveguide or wavelength of the propagating microwave, which are related to the composition of the mixture within the waveguide. While Ho, et al., mention the cutoff characteristic of a waveguide, their teaching related to cutoff is misplaced. Ho, et al. teach spacing probes along the length of a pipe at even multiple of wavelength. It is clear from their teaching to space probes an even multiple of wavelength along the length of a pipe that they do not operate in the cutoff region. In the cutoff region, the wavelength is infinite and no propagation occurs. Ho's teaching concerning probe spacing is actually a consequence of standing waves existing in the pipe in the pass band region and is not related to the cutoff phenomenon. Further, Ho's interpretation of the use of the derivative function in determining a cutoff frequency characteristic is indecorous. The maximum of the derivative function produces a precise determination of cutoff and the value of the derivative maximum is inversely related to the conductivity of the process material. Ho, et al., on the other hand, teach that one or two minima of the derivative function should be used. The first minimum is well below the cutoff frequency and is of little value in the measurement. The second minimum is above the cutoff frequency and is influenced by errors typical of other pass band measurement techniques. Use of the minima does not give a precise measurement of cutoff frequency, nor does it yield the added benefit of a conductivity measurement.

Andresen, et al., in U.S. Pat. No. 5,124,653, disclose a method and apparatus for analysis of gaseous compounds, especially for determining the concentration of a gas in a gas mixture by microwave spectroscopy. Microwave pulses are used to excite rotational transitions of the molecules in the gas compound. Andresen's method relies upon the frequency response characteristics of the molecules of the individual components of a mixture.

Jakkula, in U.S. Pat. No. 4,755,743, describes a method and apparatus for measuring the moisture content or dry content of either high or low loss materials having a moisture content in excess of 50% utilizing a dielectric waveguide in contact with the material to be measured. An amplitude measurement is made upon a pass band signal that has been reflected at least ten times.

Because of the wide presence and usage of water in industrial processes, the measurement of water content or its complement, (i.e., percent solids in a water-based slurry), is the largest user need in the analytical or composition measurement field. Almost all raw materials and finished products contain water. Measurement of this moisture content is important for custody transfer.

In industrial processing, water is often used as a product carrier through the main processing steps and later is removed during the final manufacturing stages. Water measurement is important for controlling the mixing, mechanical dewatering and thermal dewatering stages. Mixing control has a high impact on product quality and raw material usage. Also, dewatering control strongly affects energy costs and custody transfer optimization. When the final product is still in slurry form, dewatering can also have a large impact on transportation costs.

Extremely large savings are possible on many processes from only a 1 or 2 percent improvement in moisture control. The cost of acquiring the moisture measurement is not a major expenditure if a needed improvement in measurement performance can be provided.

Despite the high user need for moisture measurement, most industrial applications do not have a satisfactory measurement solution. As a result, most of the time, either the measurement is not made or it is done manually by operators taking samples to a lab where they are weighed before and after drying to determine water content. The resulting measurement-time delays prevent control optimization and cause product waste and reduced throughput.

There are many different types of sensors available for making implied percent moisture or percent solids measurement. Examples of sensors include nuclear density, coriolis density, capacitance, microwave, infrared, conductivity, light refraction, consistence meter measurement of drag force and conveyor weighing systems. Most of the sensors only sense one variable and sometimes product temperature. As a result, they only work well on binary mixtures. An additional problem is that most industrial applications have other variables, such as conductivity, pressure, inhomogenious mixing, turbulence, etc., that cause major errors in the measurement. Also, many mixtures do not provide a large contrast between water and the other material, e.g., similar specific gravity or similar refractive index. Thus, the resolution is limited and small changes in the error variables cause big changes in the moisture readings when using sensors.

The factors discussed above make it very difficult for a user to put together a custom, multisensor system to compensate for a multivariable application unless measurement design engineers are hired and provided with a large budget. Because of very large economic impact, several major companies have independently undertaken such projects to obtain microwave oil/water cut measurement systems. Also for example, a large soap manufacturer has completed a project to obtain an infrared moisture measurement of soap powder. And, because the best combination of sensors depends on the myriad of different application conditions, measurement instrument vendors have only been able to justify the design of such multisensor systems where there is a very large sales potential on a fairly repeatable process such as paper machine optimization. As a result, there is still a large, unfulfilled market demand for a moisture measurement system that can provide sufficient long-term repeatability and resolution to permit switch over from manual, off-line analysis to automatic, on-line control.

There is thus a need for a unique apparatus and method for measuring any material parameter which may be inferred by measuring the electromagnetic properties of the material.

Recognizing the need for an improved apparatus and method for measuring moisture, it is, therefore, a general feature of the present invention to provide a unique electromagnetic sensing apparatus and method for the measurement of more electromagnetic variables for more complex mixtures with less effect from other potential error sources.

A feature of the present invention is to provide a unique electromagnetic measuring apparatus and method which can be used with a liquid, a slurry or a solid mixture flowing through a conduit.

Another feature of the present invention is to provide an electromagnetic meter and method for continuous on-line measurement.

Yet another feature of the present invention is to provide an electromagnetic moisture meter and method which has improved response time, especially with respect to off line measurement.

Yet still another feature of the present invention is to provide an electromagnetic meter and method which is used without contact to and is nonintrusive with, the material being evaluated.

Another feature of the present invention is to provide an electromagnetic meter and method for measuring moisture which has a low pressure drop associated with the measurement.

Yet still another feature of the present invention is to provide an electromagnetic meter and apparatus for measuring moisture which interrogates the entire cross-section of product for measurement of all the product.

Yet another feature of the present invention is to provide an electromagnetic meter and method for measuring moisture which is continuous and online.

Yet still another feature of the present invention is to provide an electromagnetic meter and method for measuring moisture which provides superior sensitivity and selectivity.

A feature of the present invention is to provide an apparatus and method for measuring percent solids which is effective in the measurement of entrained or dissolved solid materials within a fluid.

Yet another feature of the present invention is to provide an apparatus and method for controlling blending processes, for example, the mixture of gasoline with methanol or for putting specific amounts of ether into gasoline to increase the octane.

Yet still another feature of the present invention is to provide an apparatus and method for measuring conductivity using microwaves.

Yet still another feature of the present invention is to provide an apparatus and method for measuring compositional signatures of various compounds, such as for assisting in the determination of blends of hydrocarbons.

Yet still another feature of the present invention is to provide an apparatus and method for measuring steam quality, i.e., how much liquid is present in the steam.

Yet still another feature of the present invention is to provide an apparatus and method for measuring moisture in powders, such as, for example, pneumatic conveying applications, grains, plastic pellets, pulverized coal and the like.

Yet another feature of the present invention is to provide an apparatus and method for measuring the heat value associated with certain hydrocarbons, for example, methane, butane and the like.

Yet still another feature of the present invention is to provide an apparatus and method for evaluating polar molecular gases, which evaluation would provide a measure of concentration in various materials, for example, ammonia gas.

Yet still another feature of the present invention is to provide an apparatus and method for measuring the amount of magnetic material on a surface, such as, for example, recording tape.

Yet still another feature of the present invention is to provide an apparatus and method for determining the state of cure of synthetic rubbers.

Yet still another feature of the present invention is to provide an apparatus and method for measuring the amount of water vapor in a gas atmosphere, which provides a measure of humidity, dew point and wet bulb temperature.

Even yet still another feature of the present invention is to provide an apparatus and method for determining the condensation state of a gas.

Even still another feature of the present invention is to provide an apparatus and method for the evaluation of a batch interface measurement of different substances, for example, in a pipeline.

Yet still another feature of the present invention is to provide an apparatus and method for the measurement of the thickness of sheet material, such as, for example, paper products, plastics, fibers, cloth and the like.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing features and advantages, and in accordance with the purposes of the invention as embodied and broadly described herein, a unique meter and method for the in situ measurement of the electromagnetic properties of flowable materials is provided which has superior sensitivity, selectivity and applicability.

The improved meter for the measurement of any material parameter that may be determined by knowledge of the electromagnetic properties of the material comprises a controllable electromagnetic energy source having a stable selectable frequency, a material measurement chamber having a well defined cutoff frequency response characteristic for receiving the material and for confining the electromagnetic energy from the source, a detector for accepting the energy having been influenced by the electromagnetic properties of the material in conjunction with the cutoff frequency characteristic of the measurement chamber, and a processor to control the measurement functions, set operational parameters and timing, compute necessary mathematical attributes of the frequency dependent energy, display the results, and to interface with other process instruments and equipment.

In another embodiment, a method of the present invention is provided for the measurement of a parameter of a material by measuring the electromagnetic properties of the material under investigation comprising the steps of: (a) passing material through a frequency sensitive measurement cell, (b) exposing the material to electromagnetic energy, (c) varying the frequency of the electromagnetic energy over a plurality of values to produce output with a distinct frequency shape, (d) analyzing the output to determine the cutoff frequency, (e) evaluating the cutoff characteristic, and (f) determining the parameter under investigation.

The meter apparatus of the present invention comprises a controllable source of electromagnetic energy having stable selectable frequency. The controllable source of electromagnetic energy is coupled to a material measurement chamber by means of probes, loops, antennas, apertures or other structures so as to establish an electromagnetic field inside the measurement chamber thereby causing the wave to interact with the material contained in the chamber.

The measurement chamber is configured to have a well defined frequency response characteristic such as the cutoff characteristic of a waveguide structure or a microwave filter, or other frequency dependent structure. The frequency response characteristic of the structure is affected by the electromagnetic properties of the material filling the measurement chamber which is exposed to the frequency sensitive portion of the chamber. The energy having interacted with the material in the chamber and having been influenced by the frequency dependent characteristic of the measurement chamber is coupled to a receiving circuit by probes, loops, antennas, apertures or other means to form an output. The output is amplified, detected and processed by standard means to yield a signal that contains the frequency response information in terms of the amplitude, phase, group velocity, phase velocity, or polarization characteristics of the electromagnetic field. Standard digital and analog electronic signal processing and control circuitry can be provided to control the measurement functions, set operational parameters and timing, compute necessary mathematical properties of the frequency dependent signal, display the results and to interface with other process instruments and equipment.

The frequency dependent structure, the chamber, is selected to provide a convenient means for creating a measurement space that can contain the material to be interrogated and have minimal impact upon the industrial process. The frequency dependent measurement chamber is excited with electromagnetic energy in such a way that information about the process material is encoded in the shape of a suitably selected output signal parameter.

In a simple embodiment, a hollow rectangular measurement chamber will permit material to flow through the chamber which behaves as a rectangular section of pipe or conduit from the point of view of the industrial process. A microwave signal is transmitted across the rectangular chamber with a polarization selected such that a well defined cutoff characteristic is obtained. By observing the frequency at which cutoff occurs and by observing the sharpness of this cutoff characteristic, it is possible to determine the dielectric and conductive properties of the material filling the chamber.

As appreciated by those skilled in the art, but contrary to the present invention, typical techniques use only frequencies in the passband region. Techniques outside the scope of the present invention use only the frequencies in the passband region since passband frequencies are propagating.

Propagating waves travel up and down the pipe as well as across the measurement chamber. As a consequence, disturbances from other equipment or structures within associated piping can corrupt the energy inside the measurement chamber thereby causing large errors.

Waveguides filled with highly conductive materials do not exhibit a cutoff frequency characteristic. Although the attenuation is very high, such attenuation is not due to a cutoff phenomenon. To achieve the same type of measurement for highly conductive materials as is available for low loss materials, modifications to the sample chamber are required.

An embodiment particularly useful for highly conductive materials is a variation of the hollow rectangular chamber.

As shown in FIGS. 17(a)-(c) and 18(a)-(c), insertion of a dielectric material that extends completely across the measurement chamber provides a low loss path across the chamber. The dielectric material may be placed in the center of the chamber or along one wall of the chamber such that the dielectric material extends completely across the signal path.

The highly conductive process material can then be caused to flow through the chamber such that the cutoff frequency of the waveguide comprising the upper and bottom walls of the measurement chamber, the dielectric insert partially filling the chamber and the conductive process material filling the remaining portion of the chamber will be dependent upon the electromagnetic characteristics of the process material.

In a more detailed method of the present invention, the steps for the measurement of a parameter of a material by measuring the electromagnetic properties of the material under investigation are (a) causing a material to pass through a measurement cell having a distinctive cutoff frequency characteristic, (b) exposing the material to electromagnetic energy produced by a multi-frequency source, (c) controlling the multi-frequency source so as to vary the signal frequency to produce an output in the cutoff frequency region of the measurement cell, (d) converting the output signal to a digital representation, (e) analyzing the digital representation of the signal to determine the cutoff frequency, (f) determining the sharpness of the cutoff characteristic, and (g) determining, from the measured cutoff frequency and the sharpness of the cutoff characteristic, the dielectric constant and the conductivity of the material.

It is important to note that in many cases the shape of the frequency transfer function contains sufficient information from which the dielectric and conductivity properties can be determined without the explicit need for absolute amplitude or phase measurements made with respect to any reference value. To illustrate, consider the amplitude versus frequency characteristic of an ideal parallel plate waveguide that is filled with a lossless dielectric constant, $\epsilon_r$. The waveguide structure may be excited in the so called $TE_{10}$ mode having a cutoff frequency, $f_c$. In the cutoff region, i.e., for frequencies below $f_c$, the output signal may be written as $$A(f) = A_0 \exp(-\alpha l) \quad (1)$$

where A(f) is the amplitude versus frequency of the output wave. $A_0$ is the amplitude of the input signal, l is the length of the measurement path and $\alpha$ is given as $$\alpha = \frac{\pi}{a} \sqrt{1 - (f/f_c)^2} \quad (2)$$

where a is the spacing between the waveguide plates.

Taking the natural logarithm of both sides of equation (1) and evaluating the result at two different frequencies, $f_1$ and $f_2$ gives $$\ln A(f_1) = \ln A_0 - \frac{\pi l}{a} \sqrt{1 - (f_1/f_c)^2} \quad (3)$$

$$\ln A(f_2) = \ln A_0 - \frac{\pi l}{a} \sqrt{1 - (f_2/f_c)^2} \quad (4)$$

Making amplitude measurements $A(f_1)$ and $A(f_2)$ at known frequencies $f_1$ and $f_2$ selected to be well below $f_c$ allows the unknown amplitude to be eliminated and the equations to be easily solved for $f_c$. Once $f_c$ is calculated, the unknown dielectric constant $\epsilon r$ can be found from the well known equation $$f_c = \frac{c}{2a \sqrt{\epsilon r}} \quad (5)$$

where c is the speed of light.

Another way in which $f_c$ may be found is by taking the derivative of the logarithmic function as follows.

$$\frac{d(\ln A(f))}{df} = \frac{\pi l}{a f_c^2} \frac{f}{\sqrt{1 - (f/f_c)^2}} \text{ for } f \leq f_c \quad (6)$$

Note that the derivative approaches infinity for this idealized case of a lossless mateiral as f approaches $f_c$. By observing the shape of the derivative 1 nA(f) and finding the frequency for which it achieves its maximum value, it is possible to quite accurately determine the value of $f_c$. It should be noted that while the derivative of the logarithm of the magnitude of the signal is a particularly useful mathematical transformation in identifying the cutoff frequency, $f_c$, there are many number of other such transformations that could also be used having similar useful properties that are obvious to those skilled in the art and are included in the spirit and scope of the present invention.

In actual practice, the material to be measured is never truly lossless and some modifications to equations (1) through (6) are required. However, the location along the frequency axis of the peak value of the derivative of the logarithm of the magnitude versus frequency function is still useful for determining the value of the cutoff frequency, and hence the dielectric constant, $\epsilon r$. The strength or sharpness of this peak provides a reliable measurement of the loss characteristic of the material from which the conductivity can be determined.

Other signal parameters are available for determining the value of $f_c$. These parameters also have the property that the shape of the signal parameter is sufficient for determining $f_c$. In the cutoff region, the phase shift of the energy that is coupled across the sample measurement chamber is zero. Thus, a simple relative phase measurement can be made for determining when the phase versus frequency slope achieves a nonzero value.

This phenomenon occurs at the cutoff frequency, $f_c$. Similar simple measurements can be made to determine when the phase velocity becomes infinite or when the signal group velocity goes to zero. If two polarizations are introduced to the sample chamber, a first polarization which electric field vector is parallel to the top and bottom plates of the chamber thereby exhibiting a cut-off characteristic while a second polarization whose electric field vector perpendicular to the top and bottom plates of the chamber that does not, then a simple measurement of the exiting energy polarization can be used to determine the cutoff frequency.

The measurement of the electromagnetic properties of the material can be made without the need for absolute amplitude or phase measurements.

Thus, once the electromagnetic properties of the material have been measured using shape information alone, then absolute measurements of the amplitude or phase of the energy passing through the sample will provide added dimensionality to the analysis of the characteristics of the sample material. For example, it is well known that the absolute amplitude attenuation is affected by the materials density as well as by the complex electric permittivity and magnetic permeability of the constituent materials. If the electromagnetic properties can be measured by shape information alone, then absolute measurements can be used to infer material density.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

FIGS. 1(a)-(f) illustrate the phenomenon of cutoff in a parallel-plate wave guide as practiced in the present invention;

FIG. 2 is a graph of the logarithm of the magnitude of signal versus frequency for a small value of conductivity and several values of dielectric constant as predicted by theory;

FIG. 20 is a representation of a section of a typical process installation for the invention apparatus.

Figure 3:
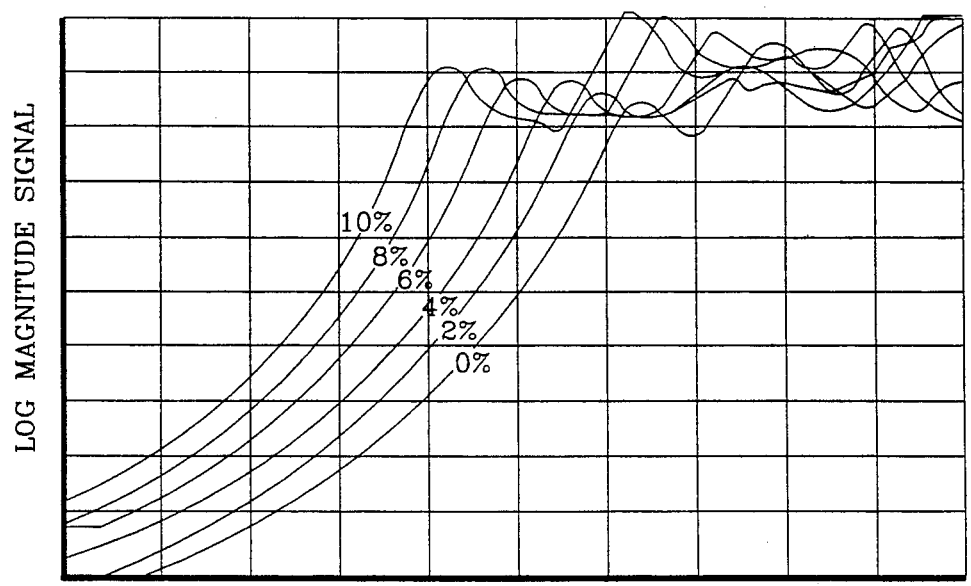
FIG. 3 is a graph illustrating the logarithm of the magnitude of signal versus frequency as practiced by the present invention in measuring water in 30 weight motor oil.

The above general description and the following detailed description are merely illustrative of the generic invention, and additional modes, advantages, and particulars of this invention will be readily suggested to those skilled in the art without departing from the spirit and scope of the invention.

DESCRIPTION OF THE PREFERRED EMBODIMENTS

Reference will now be made in detail to the presently preferred embodiments of the invention as illustrated in the accompanying drawings.

The present invention uses, in one straightforward embodiment, the characteristics of a parallel-plate wave guide having a fixed spacing between the plates. FIG. 1(a) illustrates schematically a parallel-plate wave guide having perfectly conducting plates situated in the planes $x=0$ and $x=a$. Thus, the plates have a fixed spacing a between the plates. For $TE_{m,0}$ waves guided by the plates, the following formula is applicable:

$$a = \frac{m\lambda}{2\cos\theta}$$

where λ is the free space wavelength of the microwave signal, m is the mode number and θ is the angle between the propagation vector and the vertical axis of the waveguide.

The formula can be rewritten as follows:

$$\cos\theta = \frac{m}{2a} \cdot \frac{1}{f\sqrt{\mu\epsilon}}$$

where f is the frequency, μ is the magnetic permeability and ε is the electric permeability of the medium between the plates.

Microwaves of different wavelengths or frequencies bounce obliquely between the plates. Different values of the associated angle θ make for different characteristics, for example, for high frequencies mλ/2a is small, cos θ is approximately equal to zero, and θ is approximately equal to 90 degrees. In such a case, the waves simply slide between the plates as in the case of a transmission line as shown in FIG. 1(b). As the frequency decreases, mλ/2Δ increases, θ decreases, and the waves bounce more and more obliquely as illustrated in FIGS. 1(c)-(e). Eventually the wavelength λ becomes equal to 2Δ/m for which cos θ equals 1 when θ equals zero degrees, and the microwaves simply bounce back and forth normally to the plates as illustrated in FIG. 1(f). The microwaves as illustrated in FIG. 1(f) do not illustrate any guidance by the parallel plates. For λ>2Δ/m, mλ/2Δ>1, cosθ>1 and θ has no real solution. When the microwaves bounce back and forth normally to the plates, propagation does not occur for these wavelengths in the waveguide mode. Rather, a well defined attenuation characteristic is observed based upon direct coupling of fields instead of wave propagation. Such a condition is known as the "cutoff" condition. See, for example, for further explanation the text *Elements of Engineering Electronics*, Third Ed. by Nannopameni Narayono Rao, Prentice Hall, Englewood Cliffs, N.J. 07632 (1991).

The cutoff wavelength, $\lambda_c$, is given by $$\lambda_c = \frac{2a}{m}$$

This is the wavelength for which the spacing Δ is equal to m number of one-half wavelengths. Thus, λ must be less than $\lambda_c$ for any particular mode for propagation to be possible. The cutoff frequency is given by the following:

$$f_c = \frac{m}{2a\sqrt{\mu\epsilon}}$$

Propagation of a particular mode is possible only if the frequency is greater than the cutoff frequency for that mode, i.e., λ<$\lambda_c$. Consequently, waves of a given frequency f can propagate in all modes for which the free space wavelength is less than the cutoff wavelengths or the frequency is greater than the cutoff frequencies.

FIG. 2 is a graph of the logarithm of the magnitude of signal versus frequency for a small value of conductivity and several values of dielectric constant as predicted by theory. The graph illustrates the phenomenon that the cutoff frequency is determined primarily by the value of the dieletric constant for small values of conductivity and that the shape of the logarithm of the magnitude of the signal versus frequency is of a character that enables the cutoff frequency to be easily identified. The curves in the graph of FIG. 2 were computed based upon the assumption of an ideal waveguide structure, but with the assumption that the material contained within the structure was not an ideal lossless dielectric. In actual practice, there will be features of the logarithm of the magnitude of the signal versus frequency which will depart from this ideal characteristic. However, as shown in FIG. 3, which is a graph of actual data for oil containing various amounts of water, the nature of the cutoff characteristic is the dominant frequency response characteristic and is well suited for measuring the dielectric properties of a mixture.

FIG. 3 is a graph of the logarithm of the magnitude of signal versus the frequency for water in oil samples. FIG. 3 illustrates the dominance of the cutoff frequency characteristic. In the passband region, the portion of the curves to the right of the steep sloped region, the signals are "confused." Any measure of amplitude in the passband region at any particular frequency would not yield satisfactory results in determining the amount of water in the oil. However, in the cutoff region, the region exhibiting a steep slope in the frequency response characteristic, the various curves become well behaved illustrating distinct separation as a function of the water content in the oil-water mixture. Looking for this distinct shape and determining where it occurs in frequency provides an accurate and sensitive measurement of the water content, and generally the characteristics of the mixture.

Figure 4:
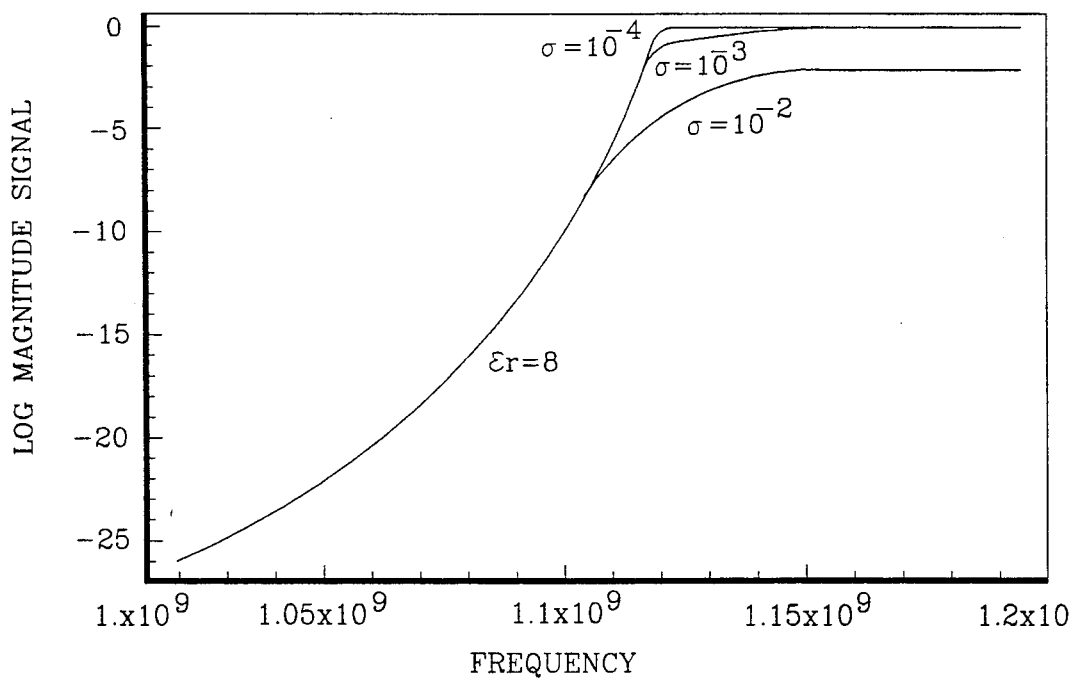
FIG. 4 is a graph of the logarithm of the magnitude of signal versus frequency for a fixed value of dielectric constant, $\xi r$, and several values of conductivity, $\sigma$, as predicted by theory.

FIG. 4 is a graph of the logarithm of the magnitude of signal versus frequency for a fixed value of dielectric constant $\epsilon_r$ and several values of conductivity σ as predicted by theory. FIG. 4 shows the theoretical behavior of the shape of the logarithm of the magnitude of the signal versus frequency as the conductivity is varied while the real part of the complex permittivity, i.e., the dielectric constant, remains fixed. The shape of the curves in FIG. 4 indicates that there is only a small change in cutoff frequency as the conductivity is changed over a fairly wide range. The sharpness of the cutoff transition region does however vary with the conductivity. Attenuation is the passband is affected as well.

Figure 5:
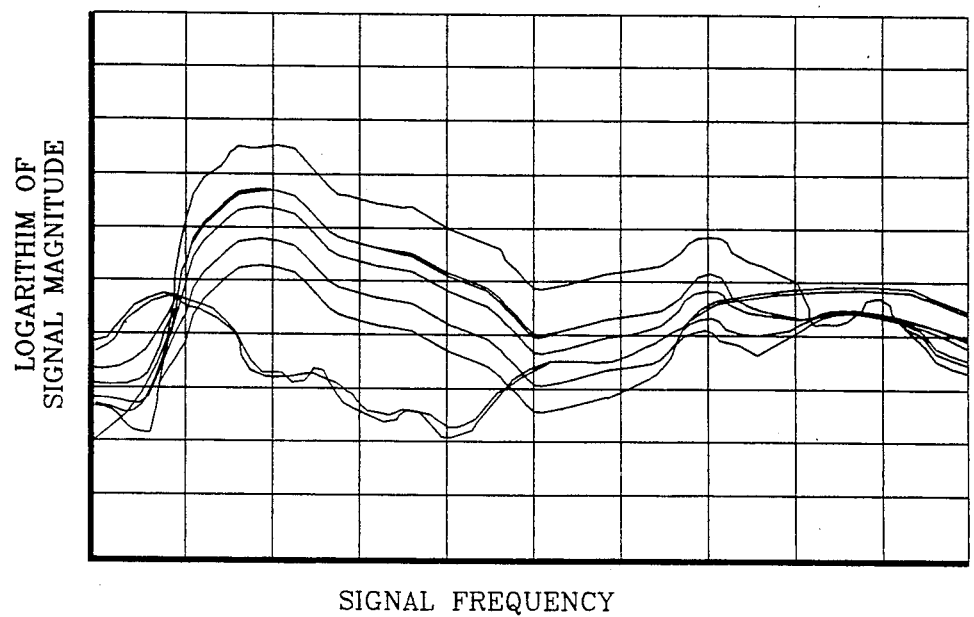
FIG. 5 is a graph illustrating the logarithm of the magnitude of signa versus frequency as practiced by the present invention in measuring salt concentration in distilled water.

FIG. 5 is a graph illustrating the logarithm of the magnitude of signal versus frequency as practiced by the present invention in measuring salt concentration in distilled water. FIG. 5 illustrates a set of actual data that were taken using distilled water and salt. As the concentration of salt dissolved in the distilled water is increased, the curves exhibit behavior similar to the theoretical results of FIG. 4. The cutoff frequency varies only slightly at the point of intersection of the exemplified curves. The cutoff frequency changes slope inversely with respect to increasing conductivity.

Figure 6:
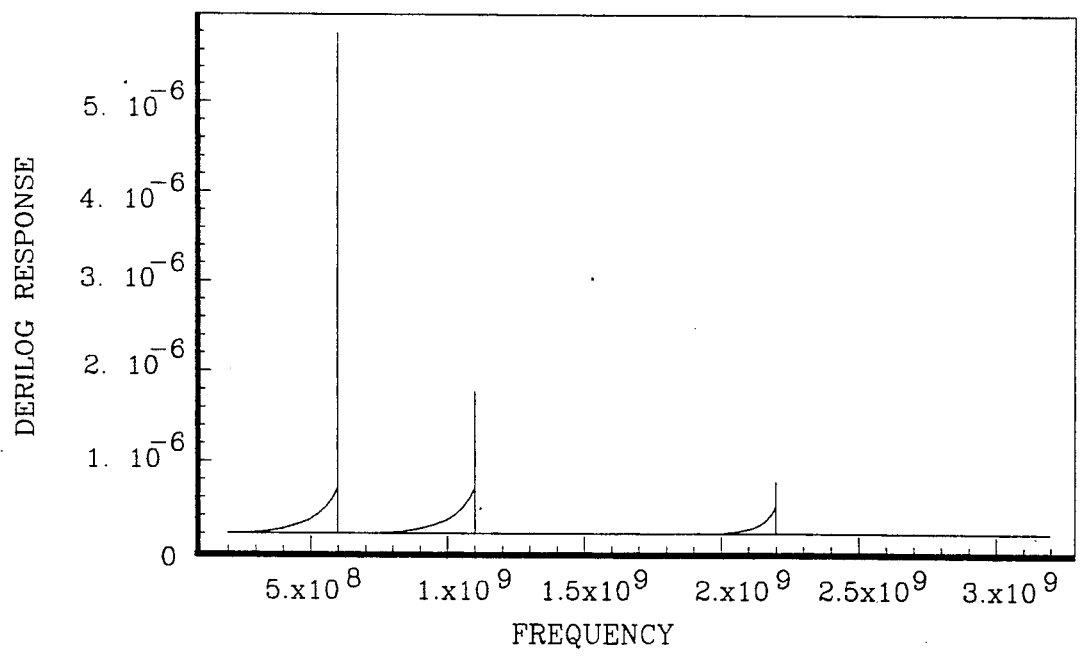
FIG. 6 is a graph of the derivative of the logarithm of the magnitude of signal versus frequency for the conditions shown in FIG. 2 illustrating that the location in frequency of the peak value of the derivative provides a measure of the cutoff frequency as predicted by theory and practiced by the present invention.

FIG. 6 is a graph of the derivative of the logarithm of the magnitude of signal versus frequency for the conditions shown in FIG. 2. FIG. 6 clearly illustrates that the location in frequency of the peak value of the derivative provides a measure of the cutoff frequency as, predicted by theory and, practiced by the present invention. FIG. 6 demonstrates theoretical results, but in this case, the derivative of the curves shown in FIG. 2 are of interest.

A very precise determination of the cutoff frequency, $f_c$, can be made by locating, along the frequency axis, the point of the function where the derivative of the logarithm of the magnitude of the signal versus frequency reaches its peak value.

Figure 7:
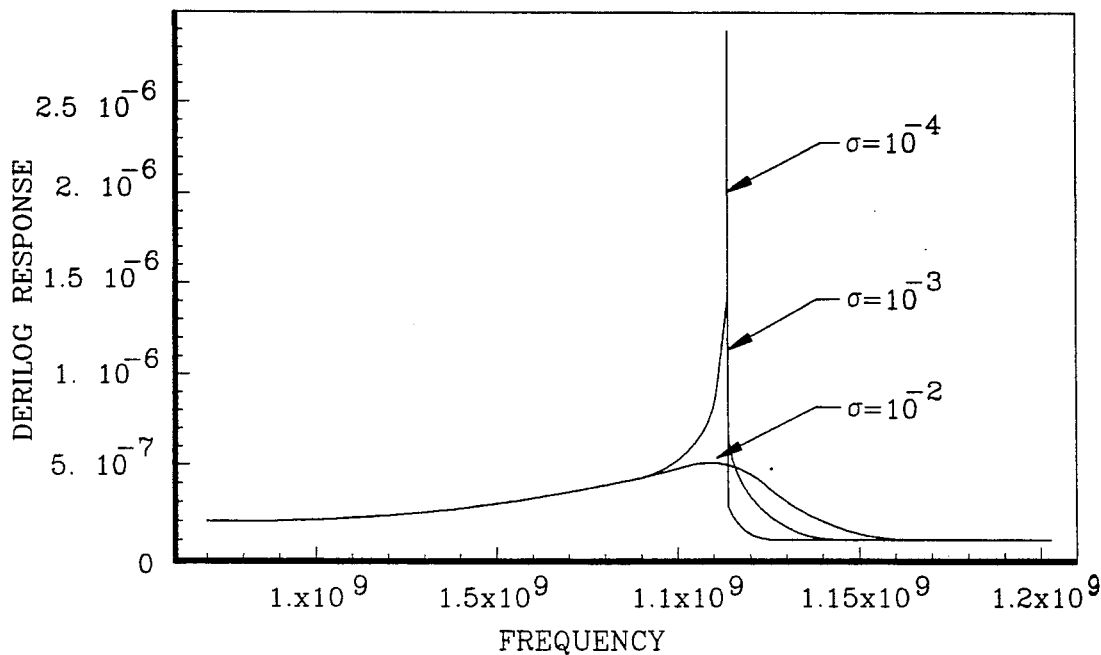
FIG. 7 is a graph of the derivative of the logarithm of the magnitude of signal versus frequency for the conditions shown in FIG. 4 illustrating that the magnitude of the derivative is inversely related to the value of the conductivity of the material whereas the location of the peak in frequency continues to provide a determination of the cutoff frequency and hence a measurement of the dielectric constant as predicted by theory and as practiced by the present invention.

FIG. 7 is a graph of the derivative of the logarithm of the magnitude of signal versus frequency for the conditions of FIG. 4. FIG. 7 illustrates that the magnitude of the derivative is inversely related to the value of the conductivity of the material and that the location of the peak in frequency provides a determination of the cutoff frequency. Thus, a measurement of the dielectric constant as predicted by theory and as practiced by the present invention are illuminated.

FIG. 7 illustrates the qualitative changes in shape of the frequency response curves transformed into quantitative results. FIG. 7 is a graph of the derivative of the curves of FIG. 4. Just as in FIG. 6, the derivatives illustrated in FIG. 7 each have a peak near the true value of $f_c$. Also important to the present invention, the height of the peaks is inversely related to the conductivity. In actual practice, the derivative function can be somewhat noisy and exhibit a number of different peaks due to such frequency sensitive parameters as amplifier gain, detector sensitivity or the like. In such noisy situations, it is desirable to make a course determination of the cutoff frequency by log-magnitude curves as shown in FIGS. 2, 3, 4, or 5 and then use the derivative function to compute a more precise value. A second derivative function can also be used to advantage, since the second derivative will cross zero at the point the first derivative reaches a peak.

Figure 8:
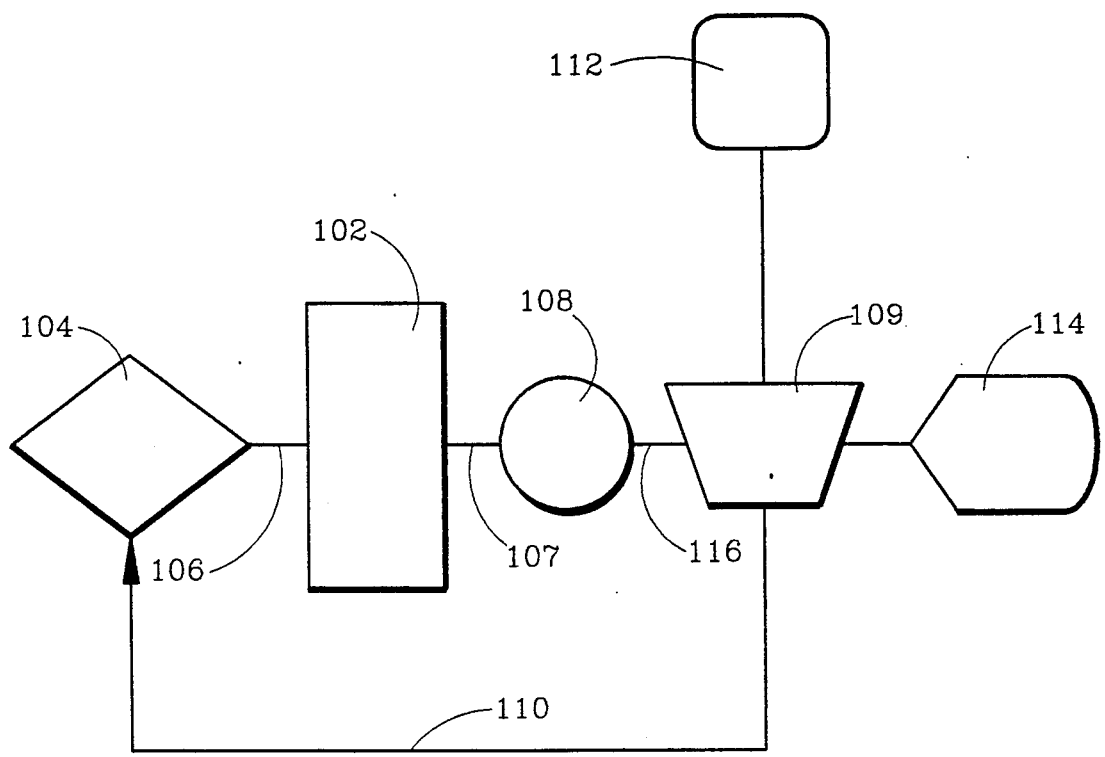
FIG. 8 is a block diagram illustrating one embodiment of the apparatus of the present invention.

FIG. 8 is a block diagram illustrating one embodiment of the apparatus of the present invention. The basic components of the invention are illuminated in FIG. 8 as a chamber 102, a multi-frequency source 104, a detector 108, a computer 109, an analog device 112, and a display 114. The multi-frequency source 104 provides a signal to the chamber 102 via a line 106. The chamber 102 has a specific dimension a as discussed above. The signal from the chamber 102 is transferred to the detector 108 via a line 107. The signal from the detector 108 is transferred to a computer 109 via a line 116. The computer 109 can provide data to an analog device 112, a display 114 or back to the multi-frequency source 104 via a line 110. It is important to note that the computer 109 functions to take the derivative of the log of the magnitudes of the signal, i.e., acts as a derilogmagnetizer.

Figure 9:
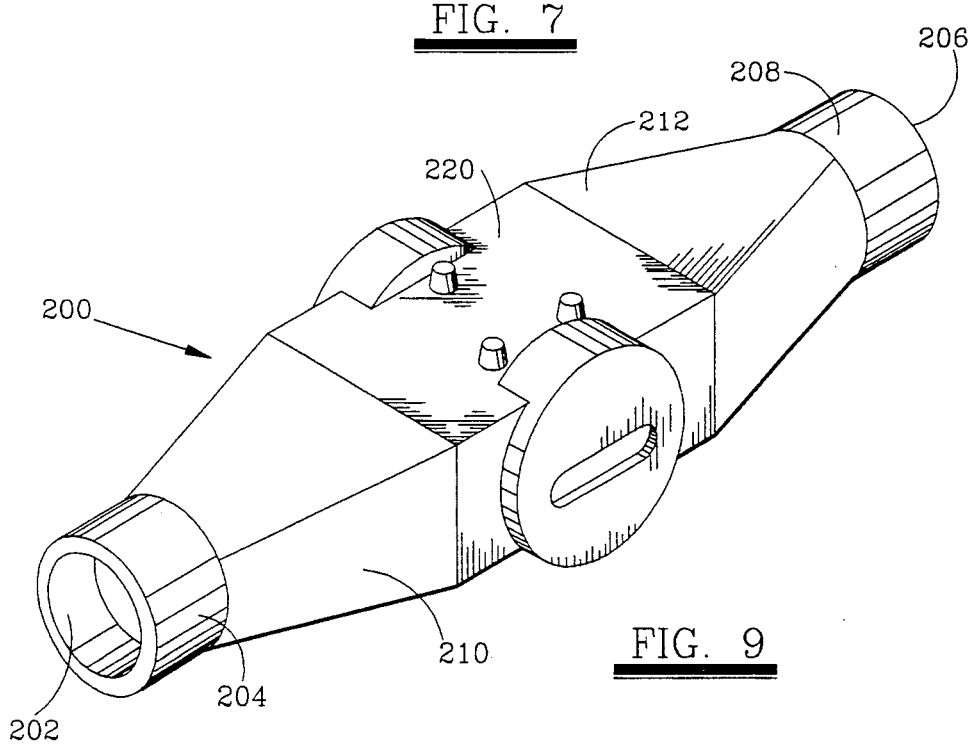
FIG. 9 is an isometric view of one embodiment of a frequency sensitive measurement cell in association with an apparatus of the present invention.

FIG. 9 is an isometric view of a preferred embodiment of a measurement chamber of the apparatus of the present invention. FIG. 9 illustrates one embodiment of the chamber 200 as represented in block diagram form in FIG. 8 (See, element 102 in FIG. 8). The chamber 200 has an intake port 202 defined by an intake collar 204. The intake collar 204 is connected to an intake transition member 210 for converting a circular cross-sectional configuration to a rectangular cross-sectional configuration. The intake transition member 210 is engaged to the measurement cell 220. The measurement cell 220 is connected to an exit transition member 212 for converting the rectangular cross-sectional configuration associated with the measurement cell 220 to a circular cross-sectional configuration. The exit transition member 212 is connected to an exit collar 208 which defines the exit port 206.

Figure 10:
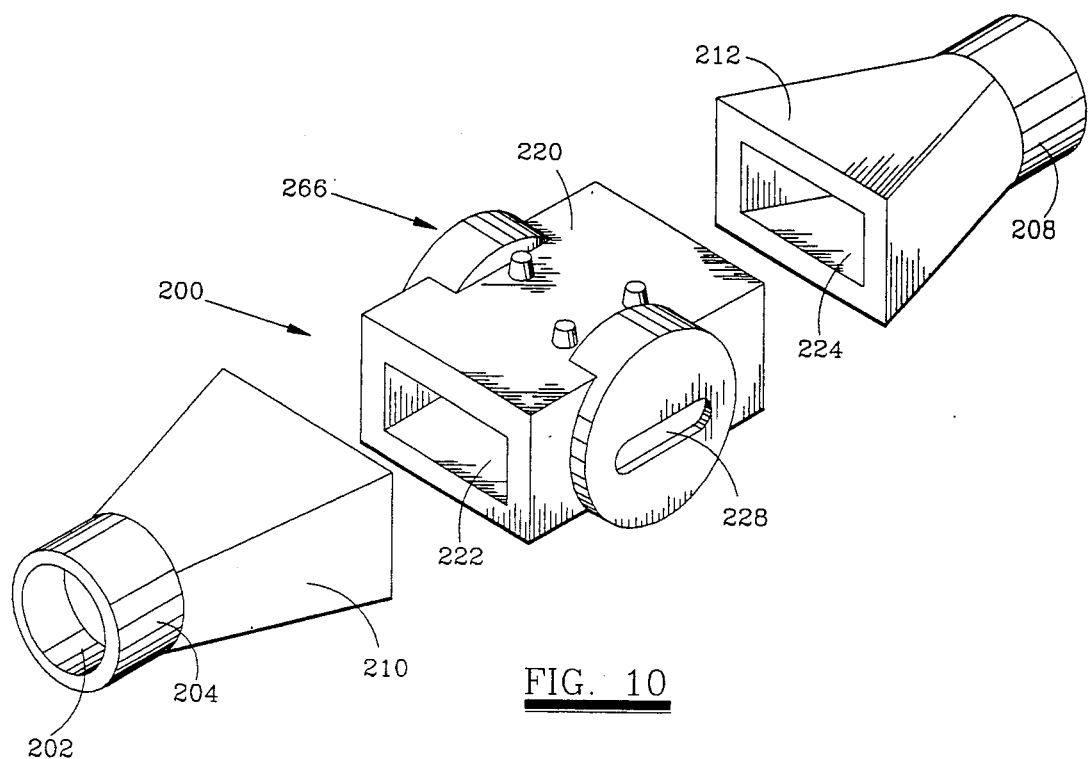
FIG. 10 is a break away isometric view of one embodiment of a frequency sensitive measurement cell in association with the apparatus of the present invention as illustrated in FIG. 9.

FIG. 10 is a break away isometric view of one embodiment of a measurement chamber in association with the apparatus of the present invention as illustrated in FIG. 9. FIG. 10 illustrates the interior characteristics of the intake transition member 210, the measurement cell 220 and the exit transition member 212. The intake transition member 210 smoothly changes, with length, in cross-sectional shape from circular to rectangular while maintaining a constant cross-sectional area. Similarly, the exit transition member 212 smoothly changes, with length, in cross-sectional shape from rectangular to circular while maintaining a constant cross-sectional area.

Processing piping couples directly to the circular intake collar 204 and exit collar 208 by means of standard pipe coupling connectors (threads, flanges, clamps, etc.) so that the measurement chamber unit 200 becomes a functional part of the process piping. Process material flowing through the process piping also flows in a continuous fashion through the measurement chamber 200 exactly as it would flow through any other section of pipe inserted in series with the process pipe line. Keeping the cross-sectional area constant minimizes the pressure drop created by inserting the chamber 200 into a process piping apparatus while assuring that voids are not created as the product material flows through the measurement cell 220.

The vertical dimension of the measurement cell 220 corresponds to dimension "a" in equation (5) for the cutoff frequency of the $TE_{10}$ mode within a parallel plate waveguide. This vertical dimension is chosen so as to cause the cutoff frequency to fall within the operable frequency range of a multi-frequency source of microwave energy 104 for the range of expected values of permittivity or permeability of the process material. The vertical dimension is also chosen such that the cutoff frequency for the $TE_{10}$ mode is greater than or equal to the cutoff frequency of the $TM_{01}$ mode that would otherwise be excited in the intake and exit collars 204 and 208 and in the process piping connected to the measurement chamber 200. The width of the measurement cell 220 is chosen such that the cross-sectional area of the measurement cell 220 is equal to the cross-sectional area of the process piping, the intake and exit collars 204 and 208, and of transition sections 210 and 212.

The measurement cell 220 has a first microwave coupling port 226 and a second microwave coupling port 228 which are parallel to each other and axially aligned. The coupling ports 226, 228 serve as entry and exit ports for the microwave energy that interacts with the material contained within the frequency sensitive measurement cell 220. In the embodiment illustrated in FIGS. 9 and 10, a coupling loop is associated with each coupling port 226, 228 for coupling energy into and out of the measurement cell 220. (See FIGS. 15 and 16). Preferably, the coupling loop or other coupling device is isolated from the interior of the measurement chamber 200. Isolation of the coupling loops from the interior of the measurement chamber 200 is readily accomplished by skilled artisans using microwave transparent windows (not illustrated).

Figure 11:
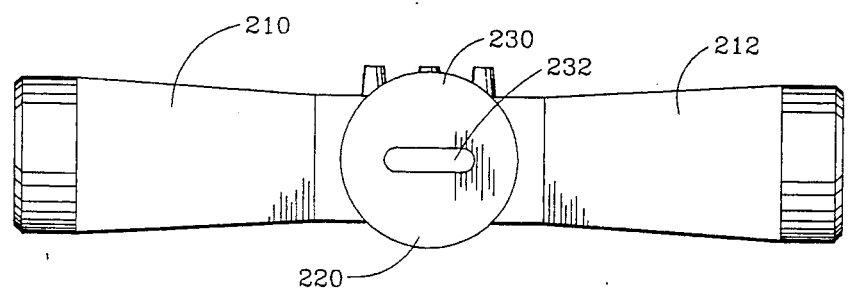
FIG. 11 is an elevation view of the isometric view of the embodiment of the frequency sensitive measurement cell of the present invention as illustrated in FIG. 9.

The frequency sensitive measurement cell 220 has an intake port 202 defined by an intake collar 204 that is connected to the intake transition member 210. Intake transition member 210 connects to a rectangular measurement cell 220 that has a well defined cutoff frequency characteristic. Similarly, exit transition member 212 is connected to the opposite side of the rectangular measurement cell 220 and to exit collar 208 which defines the exit port 206. FIG. 11 clearly illustrates via an elevation view the transition in the vertical dimension of the apparatus from the diameter of the intake and exit collars 204 and 208 to the narrow dimension of rectangular cross-section of the frequency sensitive measurement cell 220. This narrow vertical dimension, measured from the interior surfaces of the measurement cell, is the dimension that sets the cutoff frequency characteristics of the measurement cell 220.

Figure 12:
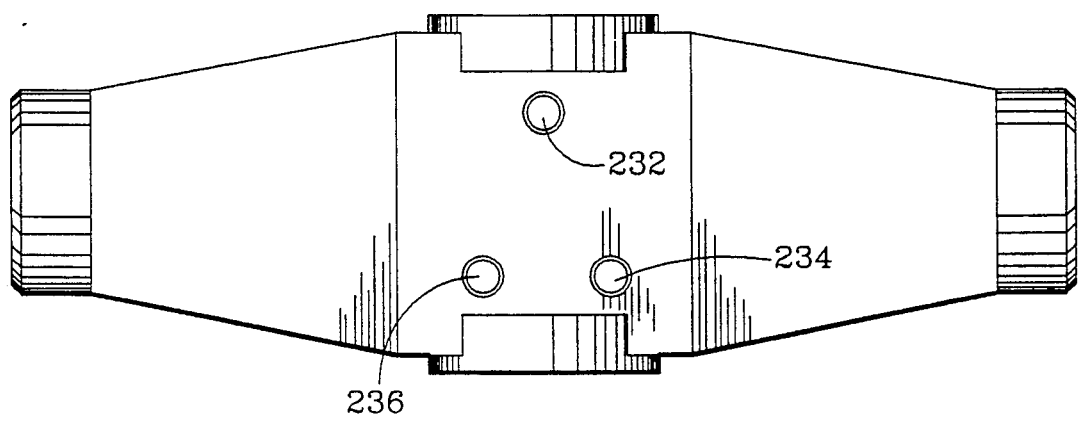
FIG. 12 is a top plan view of the isometric view of the embodiment of the frequency sensitive measurement cell of the present invention as illustrated in FIG. 9.

FIG. 12 is a top plan view of the isometric view of the embodiment of the frequency sensitive measurement chamber 220 of the present invention as illustrated in FIGS. 9 and 11. The illustrated embodiment of the frequency sensitive measurement cell 220 of the present invention is in channel alignment with respect to the passage of material therethrough. The mounting bosses 232, 234 and 236 are provided for attaching the enclosure for the microwave and electronic components associated with the invention.

Figure 13:
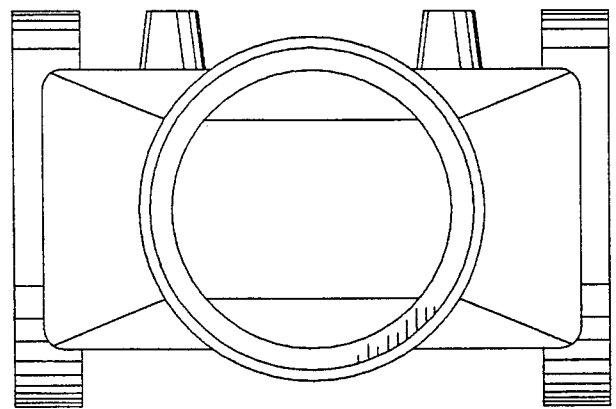
FIG. 13 is an end view of the isometric view of the embodiment of the frequency sensitive measurement cell of the present invention as illustrated in FIG. 9.

FIG. 13 is an end view of the isometric view of the embodiment of the frequency sensitive measurement chamber 220 of the present invention as illustrated in FIG. 9. The end view of FIG. 13 illustrates that the passage through the apparatus and specifically the frequency sensitive measurement cell 220. There are no protrusions or obstructions within the interior portion of the frequency sensitive measurement cell 220 that could interfere with the flow or movement of the process material through the measurement cell 230 nor are there any parts that could wear or break.

Figure 14:
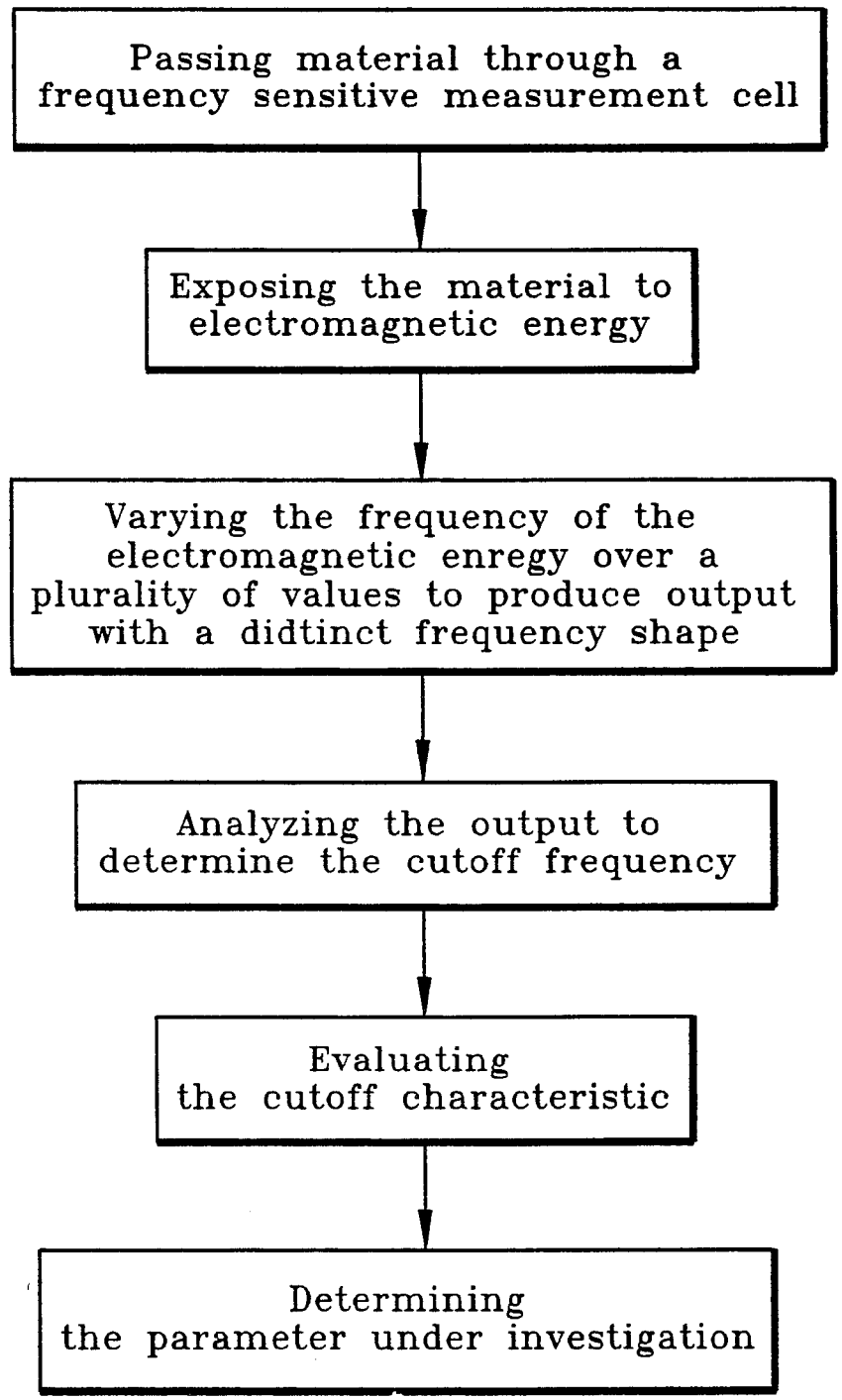
FIG. 14 is a flow diagram illustrating one embodiment of a method of the present invention.

FIG. 14 is a flow diagram illustrating the method of the present invention.

A flowable process material is pumped, blown, augered, pushed or gravity fed so as to cause it to enter, flow through and then exit a frequency sensitive measurement cell. For non-flowable process materials, the design of the frequency measurement cell must permit the process material to enter a measurement zone within the frequency sensitive measurement cell without the process material having no conform to the shape of the frequency sensitive cell. The process material is exposed to electromagnetic energy produced by a multi-frequency source. The multi-frequency source is controlled by a computer so as to vary the signal frequency in a known desired manner such that an output signal is produced having a distinctive cutoff frequency response characteristic. The output signal is detected and amplified by a receiving means and converted to a digital representation by conventional analog-to-digital conversion techniques. The digital representation of the signal is analyzed by the computer to determine the cutoff frequency of the frequency sensitive measurement cell that is defined by the geometry and materials of construction of the measurement cell and the electromagnetic properties of the process material as the process material flows through or is contained in the measurement cell. The sharpness of the cutoff characteristic is also determined by the mathematical algorithms in the computer. From the measured cutoff frequency and the sharpness of the cutoff characteristic, the dielectric constant and the conductivity of the material filling the frequency sensitive measurement cell are determined. For some applications, passband attenuation measurement may also provide an indication of material density. Using stored calibration data or equations, the computer computes and displays the desired material property, e.g., the material's moisture content. Software or hardware programs in the computer also control output transducers to send control signals to other related process equipment or data handling devices as desired. The measurement cycle is repeated at a rate consistent with the control or measurement needs of the process.

Figure 15:
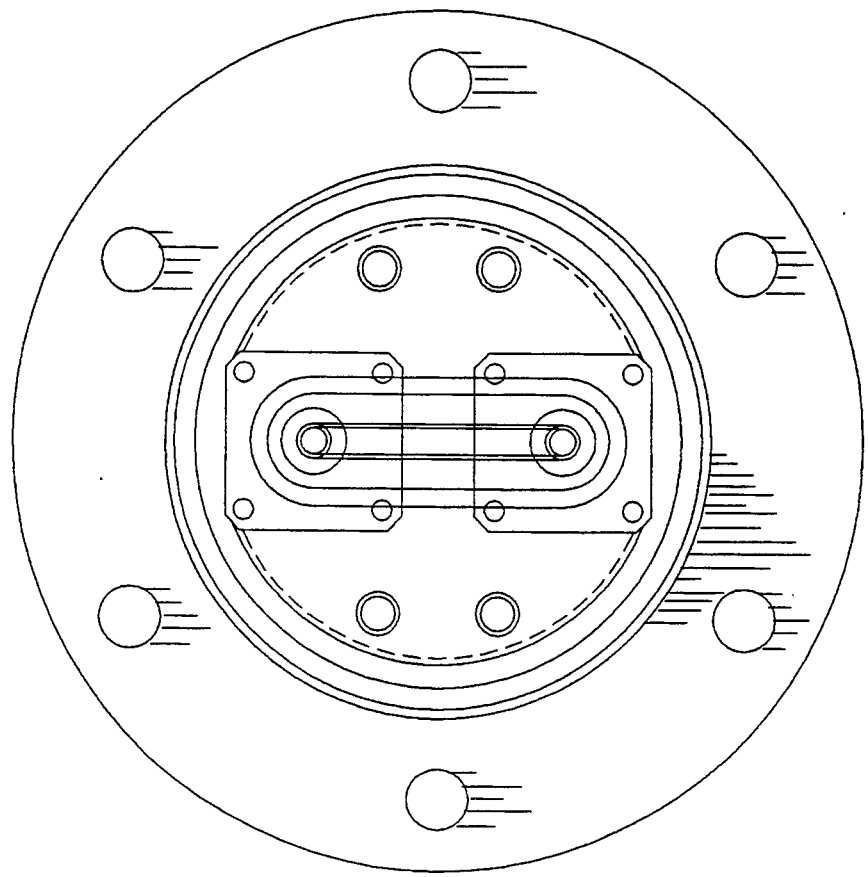
FIG. 15 is an exploded view of one embodiment of the present invention illustrating one example of loop antennas used to couple microwave energy into and out of a frequency sensitive measurement cell.

FIG. 15 is an exploded view of one embodiment of the measurement chamber 200. Shown are transmit 240 and receive 241 antenna plates that are mounted in antenna process seal adapted members 230 and 231, respectively. Openings in antenna process seal adapter members 230 and 231 form microwave coupling ports 226 and 228. Coupling ports 226 and 228 provide mounting locations for microwave transparent process seals (not shown) and housing for coupling loops 250 and 251. (Coupling loop 250 is hidden from view in FIG. 15.) Microwave energy is applied to the transmit antenna coupling loop 250 via a transmit coaxial cable 260 which connects to the multi-frequency microwave source. Energy which is coupled across the measurement chamber couples to receive antenna coupling loop 251, whereupon said energy is then communicated to the microwave energy detection means via receive coax cable 261. Coaxial cables 260 and 261 correspond to lines 106 and 107 shown in FIG. 8. The dielectric seals (not illustrated) may be contained completely within the opening in the antenna process seal adapters 230 and 231 or a single dielectric seal consisting of a continuous dielectric liner (not illustrated) may cover the entire inner surface of the measurement cell thereby sealing the openings in the antenna process seal adapters 230 and 231, or both types of dielectric seals may be used together.

Figure 16:
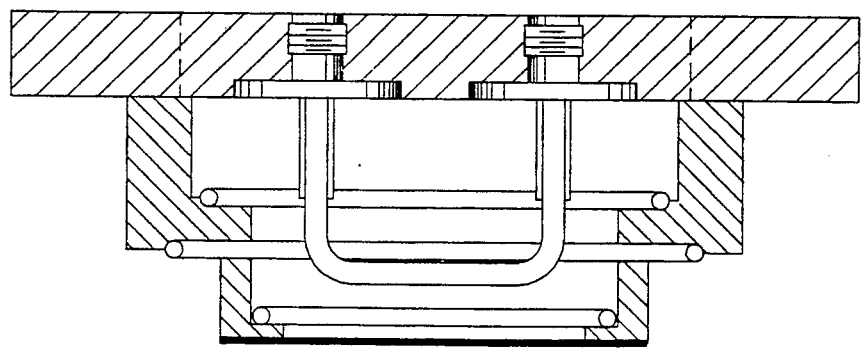
FIG. 16 is an exploded view of one embodiment of the present invention illustrating one example of the mounting of the frequency sensitive measurement chamber to the enclosure which houses the multi-frequency microwave source, the microwave detector, the computer, and the associated interface electronics.

FIG. 16 shows the arrangement for mounting the measurement chamber apparatus to the process electronics enclosure 109.

Figure 17A:
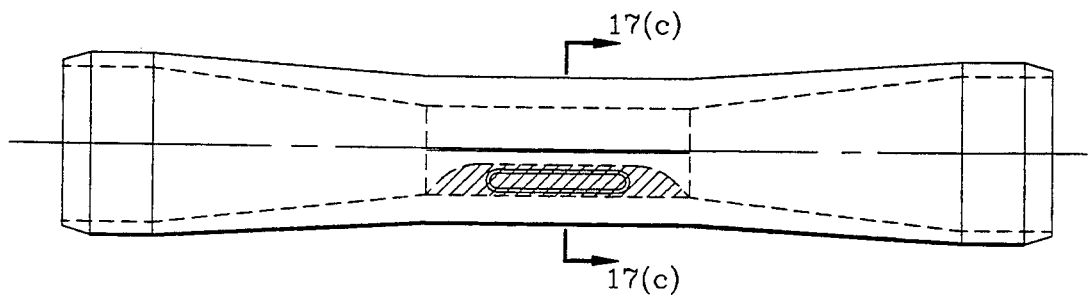
FIGS. 17(a)-(c) are isometric views of another embodiment of a measurement chamber in association with an apparatus of the present invention with a dielectric associated with one side of the chamber.
Figure 17B:
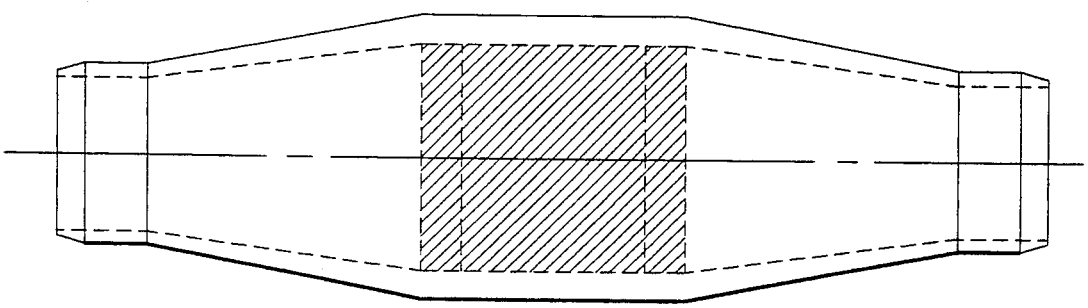
Figure 17C:
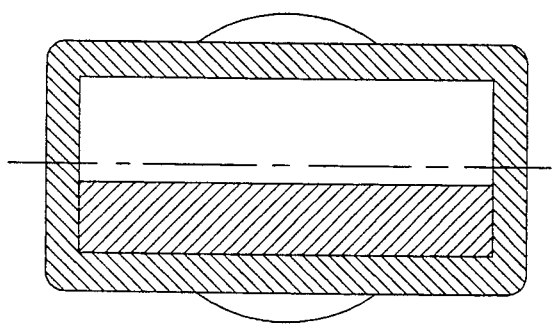

FIGS. 17(a)-(c) illustrate multiple views of alternate embodiments of a measurement cell having a well defined cutoff frequency characteristic that can be used with highly conductive process materials. As shown in FIGS. 17(a)-(c), a dielectric insert 221A is placed along one wall of the measurement cell 220A so as to provide a low loss coupling path across the measurement cell even when the remaining space in the cell is filled with a highly conductive process material. The dielectric material forms an interior portion of an effective parallel plate waveguide structure that has as one guiding plate the wall of the measurement cell 220A and as a second guiding plate the conductive material filling the measurement cell. The cutoff frequency of the resulting waveguide structure will depend upon the size of the measurement cell, the dielectric constant of the dielectric insert 221A, and the electromagnetic properties of the process material filling the remaining space in the measurement cell 220A. Note that the coupling ports (only one shown in FIG. 17(a)), corresponding to the functions of coupling ports 226 and 228 of the first embodiment shown in FIG. 9, have been shifted in position such that the microwave energy will be coupled directly into the dielectric insert 221A.

Figure 18A:
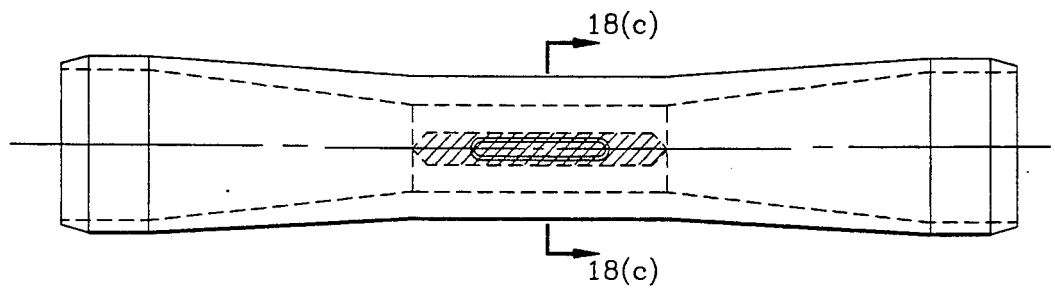
FIGS. 18(a)-(c) are isometric views of yet another embodiment of a measurement chamber in association with an apparatus of the present invention with a dielectric associated along the center of the chamber.
Figure 18B:
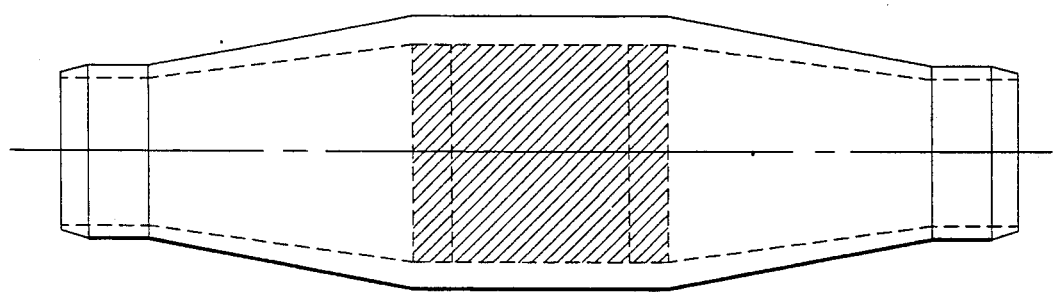
Figure 18C:
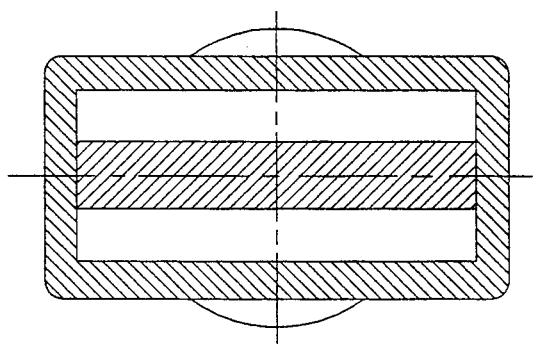

FIGS. 18(a)-(c) illustrate multiple views of yet another alternate embodiment of a measurement cell having a well defined cutoff frequency characteristic that can be used with highly conductive process materials. As shown in FIGS. 18(a)-(c), a dielectric insert 221B is placed in the center of the measurement cell even when the remaining space in the cell is filled with a highly conductive process material. The dielectric material forms an interior portion of an effective parallel plate waveguide structure that has as one guiding plate the conductive material filling the upper portion of the remaining space within the measurement cell 220B and as a second guiding plate the conductive material filling the lower portion of measurement cell 220B. The cutoff frequency of the resulting waveguide structure will depend upon the size of the measurement cell, the dielectric constant of the dielectric insert 221B and the electromagnetic properties of the process material filling the remaining space in the measurement cell 220B. Note that the coupling ports (only one shown in FIG. 18(a)), corresponding to the functions of coupling ports 226 and 228 of the first embodiment shown in FIG. 9, are positioned such that the microwave energy will be coupled directly into the dielectric insert 221B.

It is important to note that each of the embodiments presented above is best described as a parallel plate waveguide structure rather than a rectangular waveguide structure. The polarization of fields within each of the frequency sensitive measurement cells, 220, 220A and 220B is such that the electric field is parallel to the longitudinal axis of the measurement cell and therefore waves do not propagate in the axial direction down the process piping, i.e., in the direction of the flow of the process material. FIG. 20 is a representation of a section of a typical process installation for the invention apparatus. Process material enters a vat or hopper where it undergoes some process step such as mixing with water. The material is drawn out of the hopper and forced through a section of process piping and through the measurement chamber of the present invention by means of a pump or other transport mechanism. After passing through the measurement chamber the process material continues to flow through the exit piping whereupon it enters the next step of the process. Since according to the present invention, microwave energy can not propagate out of the measurement chamber and down the process piping, the measurement of the electromagnetic properties of the process material is unaffected by the presence of the pump or any other process equipment connected to the measurement chamber via the process piping. This isolation of the measurement chamber from the other process equipment by virtue of the structure of the measurement cell and transition members is a significant advantage over other methods and apparatus that seek to use the waveguide characteristics of process piping of either circular or rectangular cross-section.

Figure 19A:
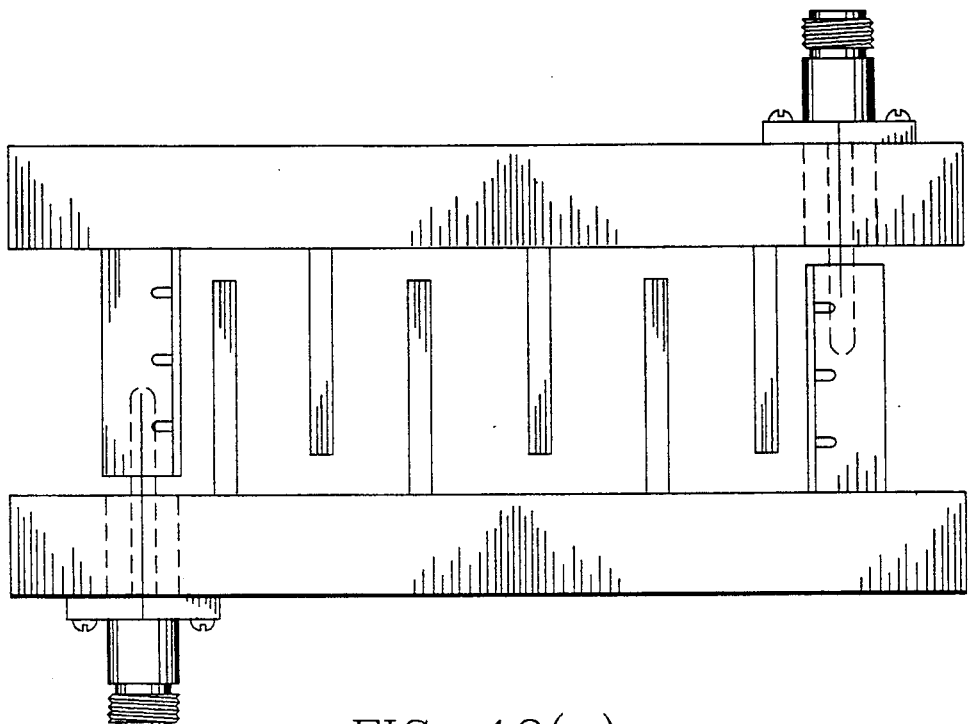
FIGS. 19(a) and (b) illustrates still another embodiment of a measurement chamber in association with an apparatus of the present invention using a plurality of resonator elements in association with the chamber.
Figure 19B:
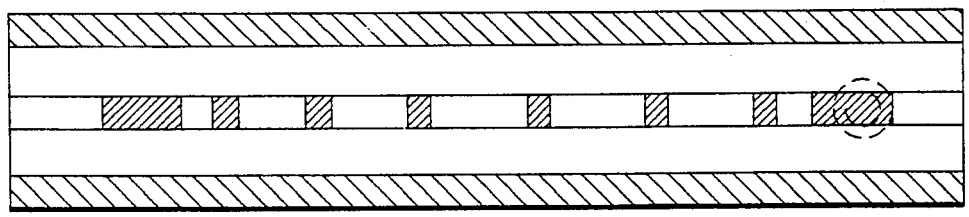

FIG. 19 illustrates another embodiment of a frequency sensitive measurement cell 220C in association with an apparatus of the present invention for use with air or gasses. The apparatus has a plurality of resonator elements or rods 221C in association with the frequency sensitive measurement cell 220C. Such a measurement cell 220C can be constructed in a similar fashion to a microwave filter but having inlet and outlet ports that permit moisture laden air or other gases to pass between the rods 221C. The presence of the moisture or other gases will alter the dielectric properties of the spaces between the rods 221C and affect the shape of the filter characteristic. Measuring the frequency response of this sample chamber will yield a measurement of the moisture content of the air or dielectric signature of other gases which may be present. The sharpness of the frequency dependent characteristic and its sensitivity to changes in dielectric and loss properties of the gases filling the spaces between the rods 221C can be controlled by the number of rods 221C, and their spacing, and by proper selection of the materials used in the construction of the chamber.

FIG. 20 is a representation of a section of a typical process installation for the invention apparatus. FIG. 20 illustrates process material moving from one processing step to the next and shows the relationship of one embodiment of the invention to other equipment in a typical process by means of the insertion of the apparatus in series with the process piping.

OPERATION

The present invention offers many operational advantages in terms of ease of use, simplicity of construction, accuracy of measurements and range of applicability. On liquid applications, the instrument can be put into service simply by replacing a section of piping with the measurement chamber. The frequency sensitive measurement cell can be made extremely rugged and robust, having the ability to withstand operating pressure in excess of 1,000 psi and temperatures greater than 450 degrees F. These pressures and temperatures can be achieved with readily available materials at very modest costs.

With respect to the frequency sensitive measurement cell 220, there are no moving parts and essentially nothing exists which can go wrong. The frequency sensitive measurement cell 220 and associated parts consists only of a stainless steel, or other suitable material, chamber 200 which smoothly transitions from a circular to a rectangular cross-section via the intake transition member 210; two nonmetallic, microwave transparent (e.g., plastic or ceramic) windows which are small, thick and flush mounted in the rectangular section; two simple coupling loops which are mounted behind the windows; and the exit transition member 212 which smoothly transitions from a rectangular to a circular cross-section via the exit transition member 212. The chamber 200 has no moving parts to fatigue, nothing protuding into the flow stream to clog or break, and no electronic components to protect.

The measurement accuracy of the present invention primarily depends upon the ability to accurately measure the cutoff frequency. The frequency sources can be made very stable and precise through the use of well known digital frequency synthesis techniques. And since the frequency calculation depends upon the shape of the frequency response characteristic rather than an absolute amplitude or phase measurement, the measurement is virtually unaffected by long term output power drift, amplifier gain shifts, detector sensitivity variations or the like.

In addition to the advantage of making a frequency measurement, the cutoff frequency approach of the present invention simplifies other aspects of the measurement that are not achieved by prior microwave measurement art. In the cutoff region, there is no propagation of energy out of the sample cell. Thus, down line disturbances are eliminated from consideration. There is also no concern with multipath propagation effects or multiple reflections from extraneous scatterers.

As the frequency approaches the cutoff region, the effective guided wavelength of the energy becomes very large. The unguided wavelength in the material is always twice as large as the vertical dimension of the sample cell at cutoff regardless of the actual cutoff frequency. As a result, the wavelength is always much larger than any air bubbles entrained in a liquid or larger than any solid particles passing through the cell. Thus, the wave is not scattered by the bubbles or particles and hence no error due to scattering can occur.

The sample chamber can be made virtually any size so as to accommodate a wide range of process materials or to place the cutoff frequency for a particular dielectric material at any value desired. While many measurement situations result in a sample cell size that places the cutoff frequency range in the microwave portion of the spectrum, the practical application of the present invention is not limited to this frequency band.

As an example of such a modification consider a frequency dependent structure similar to the construction of a microwave interdigital bandpass filter which consists of a series of resonant rods spaced apart in a parallel arrangement inside a closed housing and having alternating ends of the rods connected to electrical ground. See, FIGS. 19(a)-(b). The coupling of energy through the filter structure from rod to rod yields a precise frequency dependent transfer function. A measurement chamber can be constructed in a similar fashion to the filter but having inlet and outlet ports that permit moisture laden air or other gases to pass between the rods. The presence of the moisture or other gases will alter the dielectric properties of the spaces between the rods and affect the shape of the filter characteristic. Measuring the frequency response of this sample chamber will yield a measurement of the moisture content of the air or dielectric signature of other gases which may be present. The sharpness of the frequency dependent characteristic and its sensitivity to changes in dielectric and loss properties of the gases filling the spaces between the rods can be controlled by the number of rods and their spacing, and by proper selection of the materials used in the construction of the chamber.

Another modification in the operation of the present invention uses orthogonally polarized signals, both of which pass through the measurement cell and hence through the process material. If the measurement cell is asymmetrical in cross-section, such that the guiding structure for the two polarizations have distinct spacing or shape so as to present distinct frequency cutoff and propagation characteristics to the two orthogonal waves, then the output signals corresponding to the two polarizations may be compared to one another as a means to determine the electromagnetic properties of the material. The differences between the two polarizations in amplitude or phase will be a function of the geometry of the measurement cell and the permittivity and permeability of the process material. The advantage offered by this modification of the present invention is that a reduced frequency bandwidth can be used and yet the measurement made is still a relative measurement of amplitude or phase rather than an absolute measurement.

If the same signal source is used to generate the two polarizations, variations in output power do not affect the results. If a common receiver is used for the output signals, then shifts in receiver characteristics with time or temperature are unimportant. Since both polarizations pass through the same material sample at the same time there need be no compensation for path length differences or other factors which would affect an absolute amplitude or phase measurement approach.

Although the invention has been described in terms of the specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

Additional advantages and modification will readily occur to those skilled in the art. The invention in its broader aspects is therefore not limited to the specific details, representative apparatus, and the illustrative examples shown and described herein. Accordingly, departures may be made from the details without departing from the spirit or scope of the disclosed general inventive concept.

What is claimed is:

1. An electromagnetic property meter for the in situ measurement of any parameter of a material which may be inferred by measuring the electromagnetic properties of the material under investigation comprising:
    (a) a source for generating controllable electromagnetic energy, the energy generated by said source having stable selectable frequencies and associated wavelengths, said source operable for generating a frequency range,
    (b) a material measurement chamber in operative association with said source for receiving the energy generated by said source, said chamber having an energy confining boundary, the boundary having a coupling inlet for receiving the energy from said source into said chamber and a coupling outlet for egressing energy from said chamber, further, the boundary having dimensions so as to exhibit a cutoff condition falling within the operating limits of said source, the cutoff condition being the frequency dependent attenuation characteristic observed when the operating frequency falls below an effective cutoff frequency, the effective cutoff frequency being the frequency for which propagation ceases for an equivalent lossless material filling said chamber, such that a chamber signal is generated in said chamber representative of the material in said chamber affecting the amplitude or phase characteristics of the energy coupled across said chamber,
    (c) a detector in operative association with the coupling outlet of the boundary of said chamber for receiving the chamber signal from said chamber, said detector responsive to the chamber signal having interacted with the material in said chamber and having been influenced by the cutoff condition of said chamber such that said detector generates a detector signal which is a function of the interacted and influenced energy, and
    (d) a processor for receiving the detector signal from said detector for determining the properties of the material.

2. A method for the measurement of a parameter of a material which may be determined by measuring the electromagnetic properties of the material under investigation comprising the steps of:
    (a) generating controllable electromagnetic energy having stable selectable frequencies and associated wavelengths,
    (b) passing material through a frequency-sensitive energy-confining boundary wherein the physical dimensions of the boundary provide a cutoff condition such that propagation will not occur within the boundary and only direct coupling will occur within the boundary for a range of operating frequencies applied thereto, (c) exposing the material to electromagnetic energy over a specific frequency range having stable selectable frequencies and associated wavelengths, the frequency range corresponding to the cutoff condition thereby altering the amplitude or phase characteristics of the energy coupled across the boundary, (d) varying the frequency of the electromagnetic energy over the frequency range to ensure the electromagnetic energy is within the cutoff condition, such that a signal is produced having a distinct frequency shape corresponding to a well defined attenuation characteristic associated with the cutoff condition, the cutoff condition effected by the electromagnetic properties of the material, and (e) determining the properties of the material from the signal associated with the cutoff condition of step (d).

* * * * *